United States Patent
Rieck (10) Patent No.: US 9,694,132 B2
(45) Date of Patent: Jul. 4, 2017

(54) INSERTION DEVICE FOR INSERTION SET

(71) Applicant: MEDTRONIC MINIMED, INC., Northridge, CA (US)

(72) Inventor: Douglas A. Rieck, Venice, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 751 days.

(21) Appl. No.: 14/134,879

(22) Filed: Dec. 19, 2013

(65) Prior Publication Data

US 2015/0174319 A1 Jun. 25, 2015

(51) Int. Cl.
*A61M 5/20* (2006.01)
*A61M 5/158* (2006.01)

(52) U.S. Cl.
CPC ..... *A61M 5/158* (2013.01); *A61M 2005/1583* (2013.01); *A61M 2005/1585* (2013.01)

(58) Field of Classification Search
CPC .......... A61M 5/158; A61M 2005/1585; A61M 2005/14252; A61M 5/2033
USPC ................................ 604/135, 131, 134, 157
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, INC.

(Continued)

*Primary Examiner* — Phillip Gray
(74) *Attorney, Agent, or Firm* — Lorenz & Kopf, LLP (57) ABSTRACT

An insertion device for use with an insertion set is provided. The insertion device includes a first housing and a first member received in the first housing and movable relative to the first housing between a first position and a second position. The insertion device also includes a second housing substantially surrounding at least a portion of the first housing such that a gap exists between the first housing and the second housing. The first member is received in the gap in the second position. The second housing has at least one locking arm to couple the insertion set to the second housing. The first member is movable from the first position to the second position to uncouple the insertion set from the housing.

17 Claims, 4 Drawing Sheets

(56) References Cited

U.S. PATENT DOCUMENTS

| | | |
|---|---|---|
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,851,197 A * | 12/1998 | Marano .......... A61M 5/158 604/131 |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |

(56) References Cited

U.S. PATENT DOCUMENTS

| | | |
|---|---|---|
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2013/0060105 A1 | 3/2013 | Shah et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.

(56) References Cited

OTHER PUBLICATIONS (MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36,1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20,1988, pp. 17-20.

(56) References Cited

OTHER PUBLICATIONS

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

FIG. 4

INSERTION DEVICE FOR INSERTION SET

TECHNICAL FIELD

Embodiments of the subject matter described herein relate generally to insertion devices. More particularly, embodiments of the subject matter relate to an insertion device for an insertion set.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices require an insertion set, such as an infusion set, to be coupled to the body of a user for the delivery of the insulin. Typically, the infusion set requires a portion of a cannula, for example, to be inserted under the skin of the user to deliver the controlled amounts of insulin to the user.

In addition, in order to determine the proper amount of insulin to dispense via the manually operated syringes, insulin pens or insulin pumps, the glucose level of the user is monitored. Glucose levels may be monitored using manual devices, such as with test strips in combination with a blood glucose monitor, and/or may be monitored using an insertion set, such as a sensor set, that is coupled to a body of the user. Generally, in order to monitor glucose levels with a sensor set, at least a portion of the sensor set needs to be inserted under the skin of the user to measure glucose levels in interstitial fluid.

Accordingly, it is desirable to provide an insertion device for an insertion set for coupling the insertion set, such as an infusion set and/or a sensor set, to the body of the user. Furthermore, other desirable features and characteristics will become apparent from the subsequent detailed description and the appended claims, taken in conjunction with the accompanying drawings and the foregoing technical field and background.

BRIEF SUMMARY

According to various embodiments, an insertion device for use with an insertion set is provided. The insertion device includes a first housing and a first member received in the first housing and movable relative to the first housing between a first position and a second position. The insertion device also includes a second housing substantially surrounding at least a portion of the first housing such that a gap exists between the first housing and the second housing. The first member is received in the gap in the second position. The second housing has at least one locking arm to couple the insertion set to the second housing. The first member is movable from the first position to the second position to uncouple the insertion set from the housing.

Also provided according to various embodiments is an insertion device for use with an insertion set. The insertion device includes a first housing assembly movable between a first position, a second position and a third position. The first housing assembly including a first member coupled to a second member and a first housing. The first member is movable with the second member relative to the first housing from the first position to the second position. The insertion device also includes a second housing coupled to the first housing. The second housing includes at least one locking arm that couples the insertion set to the second housing when the first housing assembly is in the first position and the second position. The movement of the first housing assembly from the second position to the third position pivots the at least one locking arm into engagement with the first housing to uncouple the insertion set from the second housing.

Further provided according to various embodiments is an insertion device for use with an insertion set. The insertion device includes a first housing and a locking carrier disposed within the first housing and movable relative to the first housing. The insertion device includes a hub releasably coupled to the locking carrier and to the first housing to insert a portion of the insertion set. The insertion device also includes a biasing member coupled between an inner surface of the first housing and the locking carrier, and a second housing coupled to the first housing such that a gap exists between the first housing and the second housing. The second housing includes at least one locking arm that couples the insertion set to the second housing. The biasing member biases the locking carrier and the hub from a first position within the first housing to a second position. In the second position, the locking carrier is uncoupled from the hub.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description generally relates to an insertion set of the type used in treating a medical condition of a user. The insertion set can comprise an infusion set, for infusing a fluid into a body of the user, or can comprise a sensor set, for observing conditions associated with a fluid of the body of the user and generating sensor signals based thereon. The non-limiting examples described below relate to an insertion set used in the treatment of diabetes, although embodiments of the disclosed subject matter are not so limited. In alternative embodiments, however, many other characteristics may be treated by using the insertion set such as, but not limited to, various diseases, pulmonary hypertension, pain, anti-cancer treatments, medications, vitamins, hormones, or the like. For the sake of brevity, conventional features and characteristics related to insertion sets may not be described in detail here. Examples of insertion sets, such as sensor sets, used to observe and generate sensor signals based on blood glucose levels may be of the type described in, but not limited to: U.S. Patent Publication No. 2013/0060105; U.S. Pat. Nos. 5,299,571, 5,390,671, 5,482,473, 5,586,553 and 6,809,653, which are incorporated by reference herein. In addition, it should be note that although the following description is directed towards an insertion device for an insertion set, the insertion device described herein can be employed with any suitable device.

Figure 1:
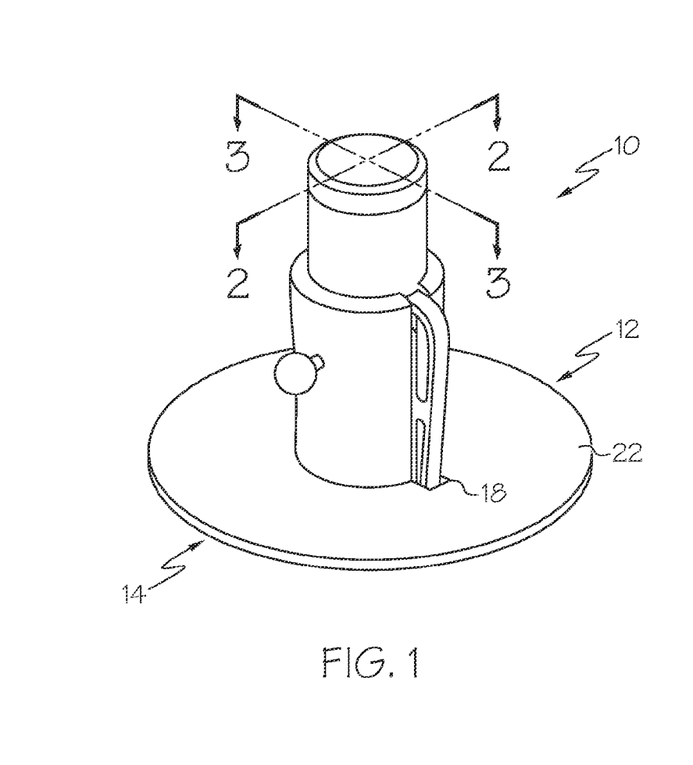
FIG. 1 is a perspective view of an exemplary embodiment of an insertion device for an insertion set according to various teachings of the present disclosure.

FIG. 1 is a perspective view of an exemplary embodiment of an insertion device 10 for coupling an exemplary insertion set 12 to a body of a user. The insertion set 12 can comprise an infusion set and/or a sensor set, which can be coupled to the body of the user by the insertion device 10 to aid in the treatment of a disease. In one example, the insertion device 10 and the insertion set 12 may be packaged together and pre-assembled to aid in coupling the insertion set 12 to the user, however, the insertion device 10 and the insertion set 12 could be packaged separately and later assembled by the user. Generally, the insertion device 10 is operated by the user to couple the insertion set 12 to the body of the user.

Figure 2:
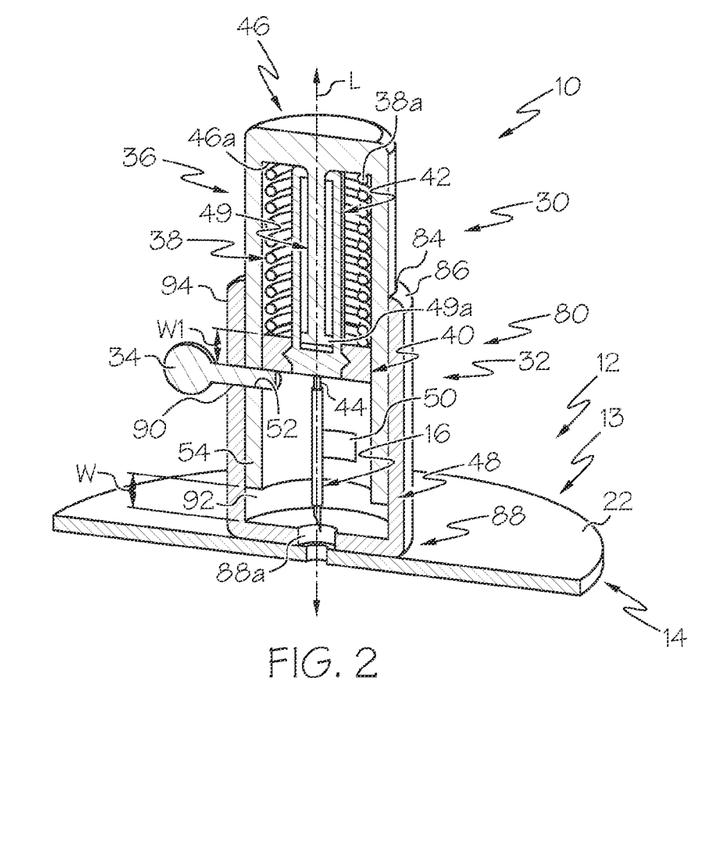
FIG. 2 is a cross-sectional view of the exemplary insertion device and insertion set of FIG. 1, taken along line 2-2 of FIG. 1.

In one of various embodiments, with reference to FIGS. 1 and 2, the insertion set 12 comprises a sensor set 13, which includes a base 14 and a sensor 16. It should be noted that the sensor set 13 illustrated herein is merely exemplary, and the sensor set 13 can include any number of additional features, including, but not limited to, a wireless transmitter, power source, cannulated tubing, etc. In one example, the sensor set 13 is any device suitable for observing glucose levels in interstitial fluid and generating sensor signals based thereon. In this example, the base 14 is illustrated herein as substantially circular, however, the base 14 may have any desired shape.

Figure 3:
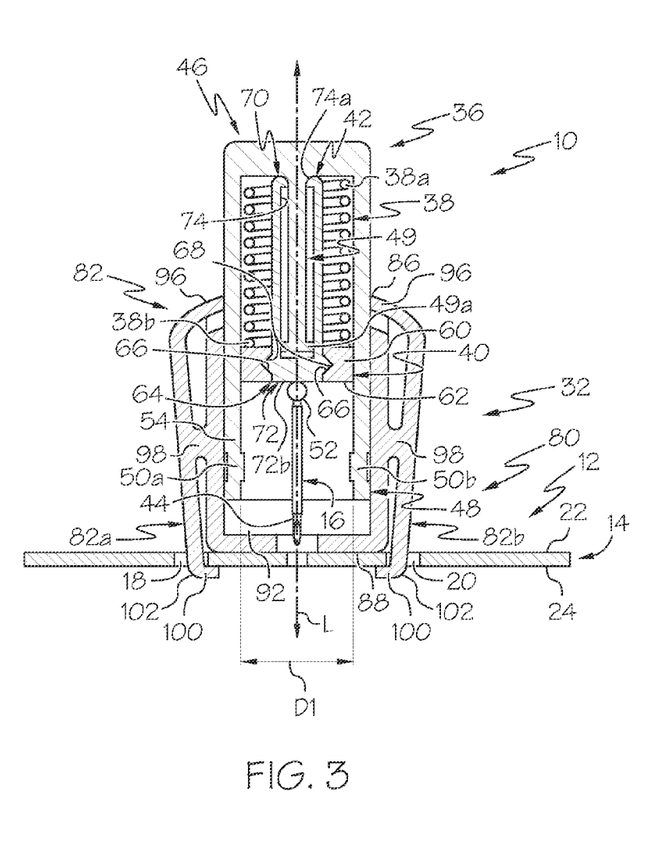
FIG. 3 is a cross-sectional view of the exemplary insertion device and insertion set of FIG. 1, taken along line 3-3 of FIG. 1, in a first position.
Figure 4:
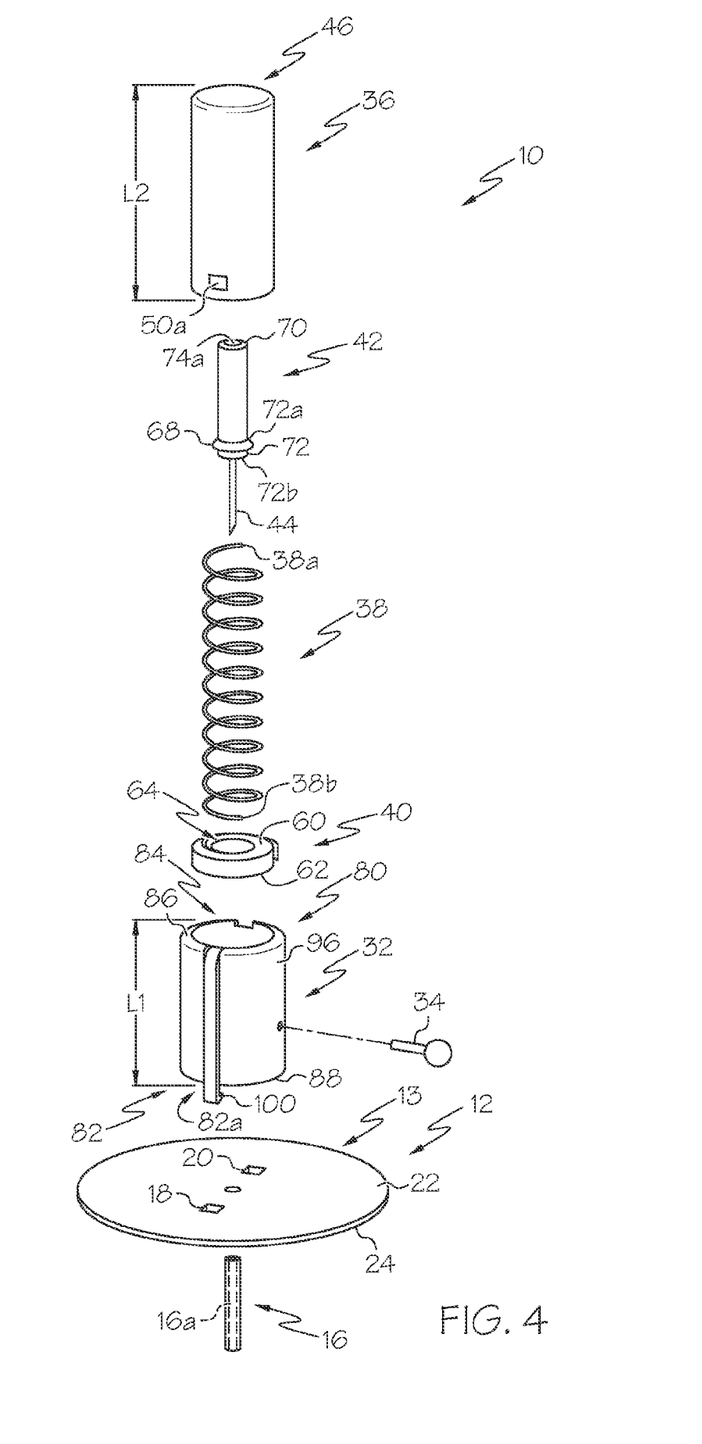
FIG. 4 is a partially exploded view of the exemplary insertion device and insertion set of FIG. 1.

With reference to FIGS. 3 and 4, the base 14 includes a first coupling aperture 18 and a second coupling aperture 20. In this example, the first coupling aperture 18 and the second coupling aperture 20 are formed substantially opposite each other about an axis of the base 14, however, as will be discussed herein, the first coupling aperture 18 and second coupling aperture 20 can be formed in any desired location on the base 14 to aid in coupling the insertion device 10 to the insertion set 12. In one example, each of the first coupling aperture 18 and second coupling aperture 20 are defined by a substantially rectangular perimeter or are substantially rectangular in shape (FIG. 4), however, the first coupling aperture 18 and second coupling aperture 20 may have any desired perimeter or shape, such as cylindrical, polygonal, etc. Furthermore, the first coupling aperture 18 and second coupling aperture 20 need not have the same perimeter or shape.

Generally, with reference to FIG. 3, the first coupling aperture 18 and second coupling aperture 20 are defined through the base 14 from a first side 22 to a second side 24 of the base 14 to facilitate the engagement of the insertion device 10 with the base 14. It should be noted, however, that the first coupling aperture 18 and second coupling aperture 20 may only be partially defined through the base 14, if desired. In addition, the second side 24 of the base 14 may also include a biocompatible adhesive to aid in coupling the base 14 to the body of the user. Further, the second side 24 of the base 14 can be coupled to a patch that includes a biocompatible adhesive to secure the base 14 to the user. The second side 24 of the base 14 can be coupled to the patch using any suitable technique, including, but not limited to, an adhesive.

In one example, the first coupling aperture 18 and second coupling aperture 20 are formed such that the sensor 16 is positioned between the first coupling aperture 18 and second coupling aperture 20. Generally, the first coupling aperture 18 and second coupling aperture 20 are substantially the same distance from the sensor 16, however, the first coupling aperture 18 or second coupling aperture 20 may be spaced a different distance from the sensor 16, if desired.

Figure 5:
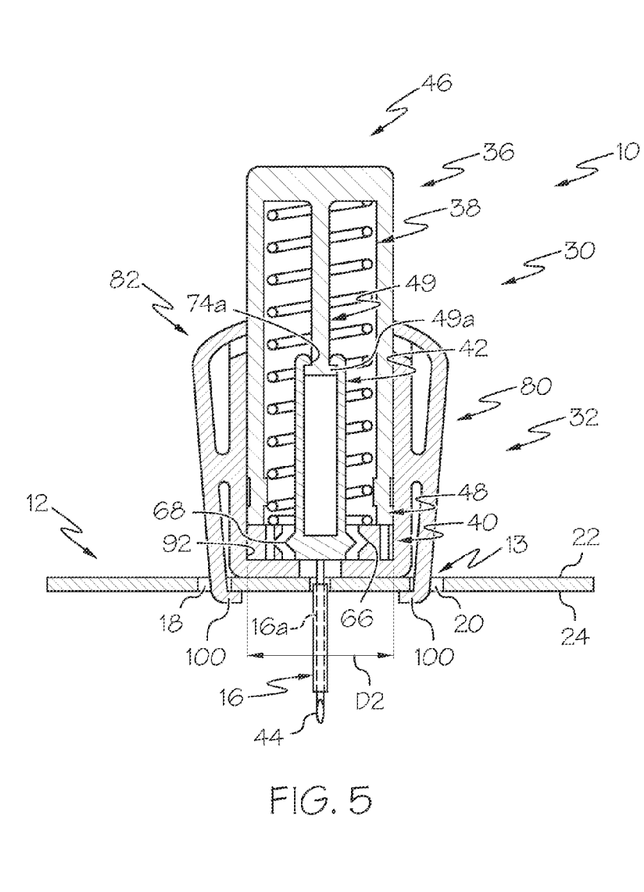
FIG. 5 is a schematic cross-sectional view of the exemplary insertion device and insertion set of FIG. 1, taken along line 3-3 of FIG. 1, in a second position.

In one of various embodiments, the sensor 16 is insertable into the body of the user to observe glucose levels in interstitial fluid of the user and generate sensor signals based thereon. In one example, as will be discussed herein, the insertion device 10 is employed to insert the sensor 16 into the body of the user at a predefined depth. Once the sensor 16 is inserted into the body of the user, the insertion device 10 may be removed and disposed of, leaving the insertion set 12 coupled to the body of the user. In one example, the sensor 16 may be formed as a cannula, and may define a throughbore 16a (FIG. 5). Sensor elements may be positioned about an internal circumference of the throughbore 16a. In addition, the throughbore 16a may receive a portion of the insertion device 10 to aid in the insertion of the sensor 16 into the body of the user, as will be discussed herein.

With reference to FIG. 2, in one of various embodiments, the insertion device 10 includes a first housing or hub housing assembly 30, a second housing or shroud 32 and a trigger 34. As will be discussed, once the trigger 34 is released, the hub housing assembly 30 moves from a first position relative to the shroud 32 along a longitudinal axis L defined by the insertion device 10 to a second position to drive the sensor 16 into the body of the user. The hub housing assembly 30 is further movable from the second position to a third position for uncoupling the insertion device 10 from the insertion set 12. In one example, the hub housing assembly 30 includes a housing 36, a biasing member 38, a first member or locking carrier 40, a second member or traveling hub 42 and an insertion instrument or needle 44. It should be noted that the hub housing assembly 30 described and illustrated herein is merely exemplary, as one or more of the components may be integrated to a single component in order to insert the sensor 16 into the body of the user.

In one example, the housing 36 is substantially cylindrical and substantially symmetrical about the longitudinal axis L. It should be noted that the shape and configuration of the housing 36 described and illustrated herein is merely exemplary, as the housing 36 can have any desired shape, such as rectangular. As will be discussed herein, the housing 36 moves relative to the shroud 32. The housing 36 includes a first end 46 and a second end 48. In one example, the first end 46 is circumferentially closed to enclose the biasing member 38, locking carrier 40, traveling hub 42 and needle 44. Generally, an inner surface 46a of the first end 46 is coupled to or adjacent an end of the biasing member 38 to act as a seat for a first end 38a of the biasing member 38.

The first end 46 also includes a rail 49, which couples the traveling hub 42 to the housing 36. In one example, the rail 49 is substantially cylindrical, and extends outwardly from the inner surface 46a of the first end 46, substantially parallel to the longitudinal axis L. The rail 49 includes a T-shaped end 49a, which cooperates with the traveling hub 42 to movably couple the traveling hub 42 to the housing 36. In this example, the traveling hub 42 may be formed about the rail 49 such that the traveling hub 42 is movable or slidable on the rail 49 to the end 49a of the rail 49. It should be noted that the shape of the rail 49 is merely exemplary, as the rail 49 may have any desired shape to constrain or limit the movement of the traveling hub 42. In addition, the placement of the rail 49 within the housing 36 is merely exemplary, as the rail 49 need not be concentric with the biasing member 38 to limit the movement of the traveling hub 42.

In one embodiment, with reference to FIG. 2, the second end 48 of the housing 36 is circumferentially open to enable the needle 44 to insert the sensor 16, as will be discussed in further detail herein. Generally, the second end 48 also includes at least one notch 50 and a trigger aperture 52. With reference to FIG. 3, the at least one notch 50 enables a portion of the shroud 32 to be coupled to the housing 36 to uncouple or release the insertion device 10 from the insertion set 12, as will be discussed herein. In this example, the second end 48 includes two notches 50a, 50b, however, the second end 48 could include any number of notches 50.

The trigger aperture 52 receives the trigger 34 to fix or lock the hub housing assembly 30 in a first position. In one example, the trigger aperture 52 is defined through a sidewall 54 of the housing 36 adjacent to the second end 48 so as to be circumferentially offset from the notches 50a, 50b (FIG. 3). It should be noted that the trigger aperture 52 is merely exemplary, as any suitable mechanism may be employed to secure the hub housing assembly 30 in the first position.

With continued reference to FIGS. 2 and 3, the biasing member 38 is coupled to the housing 36 between the inner surface 46a of the first end 46 and the locking carrier 40 so as to be compressible or expandable between the first end 46 and the locking carrier 40. In one example, the biasing member 38 is a spring, including, but not limited to, a coil spring, but it should be understood that any suitable biasing member may be employed. As will be discussed further herein, generally the biasing member 38 is compressed when the hub housing assembly 30 is in the first position.

With continued reference to FIGS. 2 and 3, and with additional reference to FIGS. 4 and 5, the locking carrier 40 is movable relative to an inner surface 54a of the sidewall 54 of the housing 36 (FIGS. 2 and 3). In one example, the locking carrier 40 is composed of a resilient material, including, but not limited to, a resilient polymeric material. The locking carrier 40 is generally movable between a first, compressed position when the locking carrier 40 is within the housing 36 (FIG. 3), and a second, expanded position when the locking carrier 40 exits the housing 36 (FIG. 5). In other words, the locking carrier 40 has a first diameter D1 in the first, compressed position (FIG. 3) and a second diameter D2 in the second, expanded position (FIG. 5), with the first diameter D1 being different than the second diameter D2. Generally, the second diameter D2 is larger than the first diameter D1. In one example, with reference to FIG. 4, the locking carrier 40 has a spiral shape, which is tightly wound in the first, compressed position and relaxed in the second, expanded position, however, the locking carrier 40 can have any desired shape, such as an accordion-like shape, for example. Furthermore, the locking carrier 40 may be press-fit into the housing 36 such that the locking carrier 40 expands when the locking carrier 40 exits the housing 36.

The locking carrier 40 has a first end 60, a second end 62 and a central bore 64 defined through locking carrier 40 from the first end 60 to the second end 62. With reference to FIG. 3, the first end 60 serves as a seat for a second end 38b of the biasing member 38. At least a portion of the second end 62 is coupled to or in contact with the trigger 34. The contact between the locking carrier 40 and the trigger 34 holds or maintains the hub housing assembly 30 in the first position. The central bore 64 receives the traveling hub 42 to couple the traveling hub 42 to the locking carrier 40 when the locking carrier 40 is in the first, compressed position. Generally, the central bore 64 includes at least one groove 66, which cooperates with corresponding at least one projection 68 of the traveling hub 42 to couple the traveling hub 42 to the locking carrier 40 when the locking carrier 40 is in the first, compressed position.

In this regard, when the locking carrier 40 is in the first, compressed position, the projection 68 of the traveling hub 42 is received and held within the groove 66 of the locking carrier 40. When the locking carrier 40 moves to the second, expanded position, with reference to FIG. 5, a diameter of the central bore 64 increases, thereby releasing the projection 68 of the traveling hub 42 from the groove 66 of the central bore 64. Stated another way, in the first, compressed position, the central bore 64 has a first bore diameter, and in the second, expanded position, the central bore 64 has a second bore diameter, which is different than the first bore diameter. As will be discussed herein, the differences between the first bore diameter and the second bore diameter enable the needle 44 to be retained and completely enclosed by the housing 36 after completion of the insertion of the sensor 16.

With continued reference to FIG. 3, the traveling hub 42 is substantially cylindrical, and includes a first end 70 and a second end 72. The first end 70 defines a bore 74 for coupling the traveling hub 42 to the rail 49 of the housing 36.

In one example, the bore 74 extends from the first end 70 to a position adjacent to the second end 72, or the bore 74 extends for such a distance to receive and enclose the rail 49. The bore 74 includes a countersink 74a at the first end 70, which can be sized to enable the traveling hub 42 to move or slide relative to a portion of the rail 49. In one example, the countersink 74a is sized such that the traveling hub 42 is movable relative to the rail 49 up to the end 49a. In other words, in this example, the countersink 74a has a smaller diameter than the end 49a of the rail 49 so that the end 49a of the rail 49 serves as a stop for further movement of the traveling hub 42. It should be noted that this configuration of the traveling hub 42 and the rail 49 is merely exemplary, as any other desired mechanisms may be employed to limit the movement of the traveling hub 42 relative to the housing 36.

The second end 72 of the traveling hub 42 is coupled to the needle 44, and includes the at least one projection 68. Generally, the second end 72 is coupled to the needle 44 such that the needle 44 is substantially parallel to the longitudinal axis L. In one example, the second end 72 is formed about an end of the needle 44 to couple the needle 44 to the traveling hub 42, however, the needle 44 may be coupled to the traveling hub 42 using any desired technique, such as ultrasonic welding, adhesives, press-fit, etc.

The projection 68 extends about at least a portion of a perimeter of the second end 72, between a proximalmost end 72a of the second end 72 and a distalmost end 72b of the second end 72. The projection 68 is sized and shaped to be received within the groove 66 of the locking carrier 40. Thus, size and shape of the projection 68 and the groove 66 are merely exemplary, as any suitable cooperating engagement features may be employed between the traveling hub 42 and the locking carrier 40 to secure the traveling hub 42 with the locking carrier 40 when the locking carrier 40 is in the first, compressed position, including, but not limited to, a dovetail arrangement.

The needle 44 comprises any suitable biocompatible needle, including, but not limited to a stainless steel surgical needle. The needle 44 is coupled to the traveling hub 42, such that movement of the traveling hub 42 along the longitudinal axis L moves the needle 44 to insert the sensor 16 into the body of the user. In one example, the needle 44 is sized such that the needle 44 may be slidably received into the throughbore 16a of the sensor 16 to aid in driving the sensor 16 into the body of the user. In this example, the needle 44 imparts rigidity to the sensor 16 during insertion, and is removable or retractable from the throughbore 16a of the sensor 16 once the sensor 16 is inserted into the body of the user.

With reference to FIGS. 2-4, the shroud 32 surrounds at least a portion of the hub housing assembly 30 and couples the insertion device 10 to the insertion set 12. The shroud 32 may be composed of any suitable material, including, but not limited to a polymeric material. In one example, the shroud 32 includes a shroud housing 80 and one or more locking arms 82 (FIG. 3).

With reference to FIG. 4, the shroud housing 80 has a length L1, which is different than a length L2 of the housing 36. Generally, the length L1 is less than the length L2 of the housing 36. The shroud housing 80 defines a central housing bore 84, which extends from a first end 86 to a second end 88, and a trigger receptacle 90. The second end 88 also defines a bore 88a to enable the needle 44 to pass through the shroud housing 80 into the body of the user. The central housing bore 84 receives at least a portion of the housing 36 so that the shroud housing 80 surrounds at least a portion of the housing 36. In one example, the central housing bore 84 can have a substantially uniform surface.

Generally, with reference to FIG. 2, the housing 36 is coupled to or received within the central housing bore 84 such that a gap 92 exists between the second end 48 of the housing 36 and the second end 88 of the shroud housing 80. The gap 92 has a width W, which may be substantially equal to or slightly larger than a width W1 of the locking carrier 40, such that the locking carrier 40 is receivable within the gap 92 in the second, expanded position (FIG. 5).

With reference back to FIG. 2, the trigger receptacle 90 may be defined through a sidewall 94 of the shroud housing 80, between the first end 86 and the second end 88. In one example, the trigger receptacle 90 defines an opening through which the trigger 34 is received. Generally, the trigger receptacle 90 is aligned substantially coaxially with the trigger aperture 52 of the housing 36 so that the trigger 34 may be positioned through the shroud housing 80 and the housing 36. It should be noted that the trigger receptacle 90 is merely exemplary, as any suitable mechanism may be employed to couple the trigger 34 to the housing 36, including, but not limited to, integrally forming the trigger 34 with the shroud housing 80.

With reference to FIG. 3, the one or more locking arms 82 may extend outwardly from the shroud housing 80. In one example, the one or more locking arms 82 includes a first locking arm 82a and a second locking arm 82b, which are formed to be substantially symmetric about the longitudinal axis L. The locking arms 82 each include a lever end 96, a support 98 and a locking tab 100.

The lever end 96 biases each locking arm 82 against the first end 86 of the shroud housing 80 in a first position and couples each locking arm 82 to the notches 50a, 50b of the housing 36 in a second position. In one example, the lever end 96 includes an arcuate shape, however, the lever end 96 may have any suitable shape. As will be discussed, the lever end 96 is movable between the first position and the second position relative to the support 98 to couple and uncouple the insertion set 12 to the insertion device 10. In the first position, when the insertion set 12 is coupled to the insertion device 10, the lever end 96 is biased against the sidewall 54 of the housing 36 and in the second position, when the insertion set 12 is uncoupled from the insertion device 10, the lever end 96 is received within the notches 50a, 50b of the housing 36.

The support 98 couples each locking arm 82 to the sidewall 94 of the shroud housing 80 and serves as a pivot point for each locking arm 82. The locking tab 100 is defined at a distalmost end 102 of each locking arm 82. The locking tab 100 generally extends for a distance beyond the second end 88 of the shroud housing 80 to pass through the first coupling aperture 18 and second coupling aperture 20 of the base 14 to couple the insertion set 12 to the insertion device 10. In one example, each locking tab 100 includes a hook-like end, which hooks onto the second side 24 of the base 14 to couple the insertion set 12 to the insertion device 10.

With reference back to FIG. 2, the trigger 34 is receivable through the trigger aperture 52 of the housing 36 and the trigger receptacle 90 of the shroud housing 80. The trigger 34 maintains the hub housing assembly 30 in the first position until the user desires to insert the sensor 16. In one example, the trigger 34 is a movable locking pin, however, the trigger 34 may comprise any suitable device, which may be separate from or integral with one or more components of the insertion device 10. For example, the trigger 34 may comprise a movable portion of the shroud 32. Thus, the trigger 34 described and illustrated herein is merely exemplary.

With reference to FIGS. 2-4, in order to assemble the insertion device 10, the biasing member 38 may be inserted into the housing 36. Then, with the needle 44 coupled to the traveling hub 42 and the sensor 16 coupled to the needle 44, the traveling hub 42 is coupled about the rail 49 and the locking carrier 40 is coupled about the second end 72 of the traveling hub 42 such that the projection 68 engages the groove 66. The locking carrier 40 is positioned in the first, compressed position and with the locking arms 82 coupled to the insertion set 12, the housing 36 is inserted into the central housing bore 84, such that the hub housing assembly 30 is in the first position. Then, the trigger 34 may be inserted through the trigger receptacle 90 and trigger aperture 52 to retain the hub housing assembly 30 in the first position.

With the insertion set 12 coupled to the insertion device 10, in order to couple the insertion set 12 to the user, the second side 24 of the base 14 of the insertion set 12 may be secured to the user, using an adhesive or a patch, for example. Then, in order to insert the sensor 16, the trigger 34 may be at least partially removed. The removal of the trigger 34 from the trigger aperture 52 releases the compressed biasing member 38, which moves or biases the hub housing assembly 30 from the first position (FIG. 3) to the second position (FIG. 5). In other words, the once the trigger 34 is removed from at least the trigger aperture 52, the traveling hub 42 and the locking carrier 40 move from a position adjacent to the first end 46 of the housing 36 to a position beyond the second end 48 of the housing 36. The movement of the traveling hub 42 to the position beyond the second end 48 of the housing 36 causes the needle 44 to insert the sensor 16 into the user.

Figure 6:
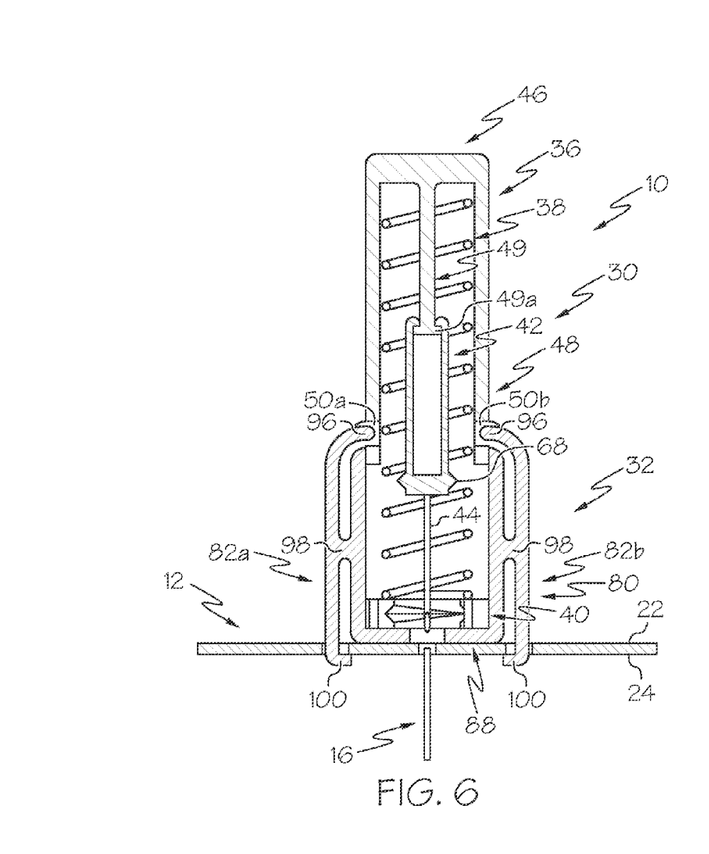
FIG. 6 is a schematic cross-sectional view of the exemplary insertion device and insertion set of FIG. 1, taken along line 3-3 of FIG. 1, in a third position.

In the second position, as illustrated in FIG. 5, the countersink 74*a* of the traveling hub 42 of the hub housing assembly 30 is in contact with the end 49*a* of the rail 49, and the locking carrier 40 is received within the gap 92. As the gap 92 has a diameter larger than a diameter of the housing 36, the locking carrier 40 moves into the second, expanded position in the gap 92. Thus, the release of the trigger 34 causes the locking carrier 40 to move from the first, compressed position to the second, expanded position. The movement of the locking carrier 40 from the first, compressed position to the second, expanded position causes the groove 66 of the locking carrier 40 to disengage the projection 68 of the traveling hub 42. With the traveling hub 42 uncoupled or released from the locking carrier 40, the recoil of the biasing member 38 from contacting the locking carrier 40 with the second end 88 of the shroud housing 80, moves or drives the housing 36 upward, away from the shroud housing 80 to move the hub housing assembly 30 to the third position as illustrated in FIG. 6. The movement of the housing 36 upward, away from the shroud housing 80, moves the traveling hub 42 upward, away from the shroud housing 80 and retracts the needle 44 from the throughbore 16*a* of the sensor 16 into the shroud housing 80.

Figure 7:
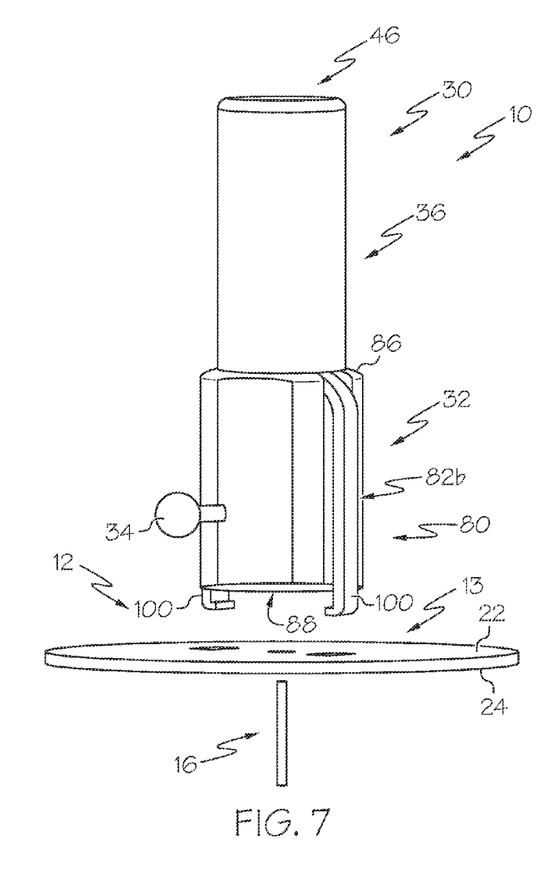
FIG. 7 is a perspective view of the exemplary insertion device uncoupled from the insertion set of FIG. 1.

With continued reference to FIG. 6, during the movement of the hub housing assembly 30 to the third position, the locking arms 82 pivot and engage the notches 50*a*, 50*b* of the housing 36. The engagement of the locking arms 82 with the notches 50*a*, 50*b* moves the locking tabs 100 out of engagement with the second side 24 of the base 14 of the insertion set 12, which enables the insertion device 10 to be removed from the insertion set 12 (FIG. 7). In addition, the engagement of the locking arms 82 with the notches 50*a*, 50*b* locks the housing 36 relative to the shroud housing 80. With the housing 36 in the third position, the needle 44 is fully contained within the housing 36 and shroud housing 80, enabling proper disposal of the insertion device 10 (FIG. 6).

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An insertion device for use with an insertion set, comprising:
   a first housing;
   a first member received in the first housing and movable relative to the first housing between a first position and a second position; and
   a second housing substantially surrounding at least a portion of the first housing such that a gap exists between the first housing and the second housing, with the first member received in the gap in the second position, the second housing having at least one locking arm to couple the insertion set to the second housing, and the first member is movable from the first position to the second position to uncouple the insertion set from the second housing,
   wherein the at least one locking arm includes a lever end pivotable to engage the first housing when the first member is in the second position and an engagement of the at least one locking arm with the first housing uncouples the insertion set from the second housing.

2. The insertion device of claim 1, wherein in the first position, the first member has a first diameter, and in the second position, the first member has a second diameter, with the first diameter different than the second diameter.

3. The insertion device of claim 1, further comprising:
   a second member coupled to the first housing and to the first member in the first position,
   wherein, in the second position, the second member is uncoupled from the first member.

4. The insertion device of claim 3, wherein the second member includes a first end and a second end, with a bore defined through the first end that slidably receives a rail of the first housing, and the second end is coupled to the first member.

5. The insertion device of claim 3, further comprising:
   a biasing member disposed within the first housing between a first end of the first housing and the first member.

6. The insertion device of claim 5, further comprising:
   a trigger that retains the first member in the first position, wherein the biasing member is compressed in the first position.

7. The insertion device of claim 1, wherein the insertion set is selected from the group consisting of an infusion set and a sensor set.

8. An insertion device for use with an insertion set, comprising:

an assembly movable between a first position, a second position and a third position, the assembly including a first member coupled to a second member and a first housing, the first member movable with the second member relative to the first housing from the first position to the second position; and a second housing coupled to the first housing, the second housing including at least one locking arm that couples the insertion set to the second housing when the assembly is in the first position and the second position, wherein movement of the assembly from the second position to the third position pivots the at least one locking arm into engagement with the first housing to uncouple the insertion set from the second housing, the at least one locking arm includes a lever end pivotable to engage the first housing when the assembly moves from the second position to the third position, and an engagement of the at least one locking arm with the first housing uncouples the insertion set from the second housing.

9. The insertion device of claim 8, wherein the second housing is coupled to the first housing such that a gap exists between the first housing and the second housing, and the first member is receivable within the gap in the second position.

10. The insertion device of claim 9, wherein the second member is releasably coupled to the first member, and the second member is uncoupled from the first member in the second position.

11. The insertion device of claim 10, wherein the first member has a spiral shape.

12. The insertion device of claim 8, wherein the second member includes a first end and a second end, with a bore defined through the first end that slidably receives a rail of the first housing to couple the second member to the first housing, and the second end of the second member is coupled to the first member.

13. The insertion device of claim 12, further comprising an insertion instrument coupled to the second end of the second member.

14. The insertion device of claim 8, wherein the insertion set is selected from the group consisting of an infusion set and a sensor set.

15. The insertion device of claim 8, further comprising:
a biasing member disposed within the assembly between a first end of the first housing and the first member.

16. An insertion device for use with an insertion set, comprising:
a first housing;
a locking carrier disposed within the first housing and movable relative to the first housing;
a hub releasably coupled to the locking carrier and to the first housing to insert a portion of the insertion set
a biasing member coupled between an inner surface of the first housing and the locking carrier; and
a second housing coupled to the first housing such that a gap exists between the first housing and the second housing, the second housing including at least one locking arm that couples the insertion set to the second housing,
wherein the biasing member biases the locking carrier and the hub from a first position within the first housing to a second position and in the second position the locking carrier is uncoupled from the hub; and
wherein the at least one locking arm includes a lever end pivotable to engage the first housing when the locking carrier is in the second position and an engagement of the at least one locking arm with the first housing uncouples the insertion set from the second housing.

17. The insertion device of claim 16, further comprising:
a trigger that retains the locking carrier in the first position,
wherein the biasing member is compressed in the first position.

* * * * *